United States Patent
Lin et al.

(10) Patent No.: US 7,193,698 B2
(45) Date of Patent: Mar. 20, 2007

(54) WAFER DEFECT DETECTION METHODS AND SYSTEMS

(75) Inventors: Long-Hui Lin, Hsinchu County (TW); Li-Yu Chan, Hsinchu (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 49 days.

(21) Appl. No.: 11/182,798

(22) Filed: Jul. 18, 2005

(65) Prior Publication Data
US 2007/0013900 A1     Jan. 18, 2007

(51) Int. Cl.
*G01N 21/00* (2006.01)

(52) U.S. Cl. .............. 356/237.3; 356/237.2; 356/237.4; 356/237.5

(58) Field of Classification Search ........... 356/614, 356/239.8, 401, 399, 386, 493, 485, 237.2, 356/237.3, 237.4, 237.5; 382/145, 144
See application file for complete search history.

(56) References Cited

U.S. PATENT DOCUMENTS

| 5,847,821 A | * | 12/1998 | Tracy et al. | ............. 256/237.1 |
| 6,559,457 B1 | * | 5/2003 | Phan et al. | ............. 250/491.1 |
| 2003/0145291 A1 | * | 7/2003 | Fujii et al. | ............. 716/4 |

* cited by examiner

*Primary Examiner*—Akm Ullah
*Assistant Examiner*—Rebecca C. Slomski
(74) *Attorney, Agent, or Firm*—Birch, Stewart, Kolasch, and Birch, LLP

(57) ABSTRACT

A wafer detection method. A plurality of PSL particles are sprayed on a wafer. An inspection operation is implemented on the wafer to obtain location information corresponding to a plurality of defects on the wafer, each location information corresponding to the defects comprises an error value. An inspection operation implemented on the PSL particles to obtain location information corresponding to the PSL particles. Offset location information corresponding to each defect is calculated according to the location information corresponding to each PSL particle. The error values corresponding to each defect are corrected according to the offset location information corresponding to each defect.

9 Claims, 4 Drawing Sheets

WAFER DEFECT DETECTION METHODS AND SYSTEMS

BACKGROUND

The invention relates to defect detection methods, and more particularly, to discover defect locations by spraying locating particles on a wafer.

In semiconductor manufacturing, wafers are inspected to discover defects using inspection tools during etching, developing, deposition, and other processes. As critical dimensions for semiconductor processes are gradually decreased and precision and accuracy for wafer inspection are progressively increased. To confirm product quality, high resolution optical instruments for integrated circuit (IC) manufacture/design must be employed to implement inspection processes. These processes comprise inspection after etching (AEI), inspection after developing (ADI), quality assurance (QA), quality control (QC), and others.

Wafer inspection mainly locates defects on a chip. Conventional wafer probe tests comprise testing related electrical characteristics of all memory cells (arrayed in a matrix) on a chip, displaying coordinates of failed memory cells in the form of fail bit mapping (FBM), according to test results, in a coordinate region defined by X and Y axes, and estimating failure reasons according to analyzed FBM types, such as point-fail, block-fail, or line-fail. Fail bit mapping is an abnormal analysis method for semiconductor components, visualizing addresses of abnormal memory cells for confirmations.

Additionally, conventional wafer inspection methods further inspect wafers using an optical microscope, a scanning electron microscope (SEM), or a transmission electron microscope (TEM). The described microscopes are widely employed in wafer and mask inspection and further employed in crystal liquid display (LCD), compact discs, hard discs, QC and process management applications, nanotechnology, micro-electro-mechanical systems, and others.

Current inspection methods, however, have reached a bottleneck, and are incapable of further re-detection when extremely small (less than 100 nm) particles or defects on wafers are detected, particularly for unpatterned wafers. When extremely small (10 nm or less) particles or defects are detected, unpatterned wafers are employed to improve yields. Tiny defects, however, affect critically, such that defect re-detection is important. Additionally, different tool settings (alignment coordinates, for example) may reduce the success rate for re-detection.

Thus, an improved wafer defect detection method for extremely small particles or defects is desirable.

SUMMARY

Wafer defect detection methods are provided. In an embodiment of such a method, multiple locating particles are sprayed on a wafer. An inspection operation is implemented on the wafer to obtain location information corresponding to a plurality of defects on the wafer. Each location information corresponding to the defects comprises an error value. An inspection operation is implemented on the locating particles to obtain location information corresponding to the locating particles. Offset location information corresponding to each defect according to the location information corresponding to each locating particle are calculated. Error values corresponding to each defect according to the offset location information corresponding to each defect are corrected.

Also disclosed are wafer defect detection systems. An embodiment of such a system comprises a particle spraying unit, a defect detection unit, a particle detection unit, and a particle re-detection unit. The particle spraying unit sprays a plurality of locating particles on a wafer.

The defect detection unit implements an inspection operation on the wafer to obtain location information corresponding to a plurality of defects on the wafer, each location information corresponding to the defects comprises an error value. The particle detection unit implements an inspection operation on the locating particles to obtain location information corresponding to the locating particles. The particle re-detection unit calculates offset location information corresponding to each defect according to the location information corresponding to each locating particle, and corrects error values corresponding to each defect according to the offset location information corresponding to each defect.

BRIEF DESCRIPTION OF THE DRAWINGS

The invention can be more fully understood by reading the subsequent detailed description and examples of embodiments thereof with reference made to the accompanying drawings, wherein.

DETAILED DESCRIPTION

The invention discloses a wafer defect detection method and system.

A wafer defect detection method of the invention detects, but is not limited to, extremely small (less than 100 nm) particles or defects on wafers.

Figure 1:
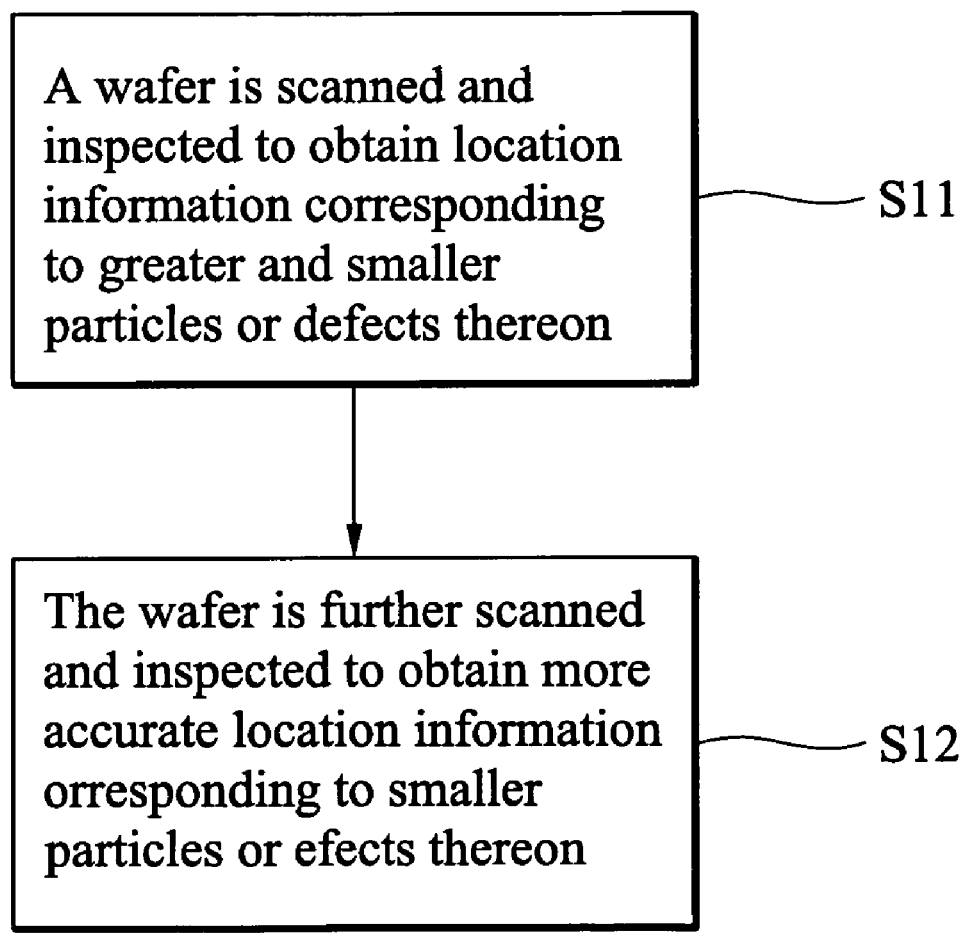
FIG. 1 is a flowchart of a conventional wafer defect detection method.

As described, conventional defect detection methods can detect greater size particles or defects on wafers. FIG. 1 is a flowchart of a conventional wafer defect detection method. A wafer is scanned and inspected to obtain location information corresponding to particle or defect size on the wafer (step S11). The wafer is further scanned and inspected to obtain more accurate location information corresponding to smaller size of particles or defects on the wafer (step S12). Due to hardware limitations, smaller particles or defects on the wafer cannot be accurately located within an error value range between 50 um ~200 um, thus repairs cannot be implemented.

A wafer defect detection method detects relative locations of tiny particles or defects on a wafer using polystyrene latex (PSL) particles, thereby obtaining correct location information corresponding to the tiny particles or defects.

Figure 2:
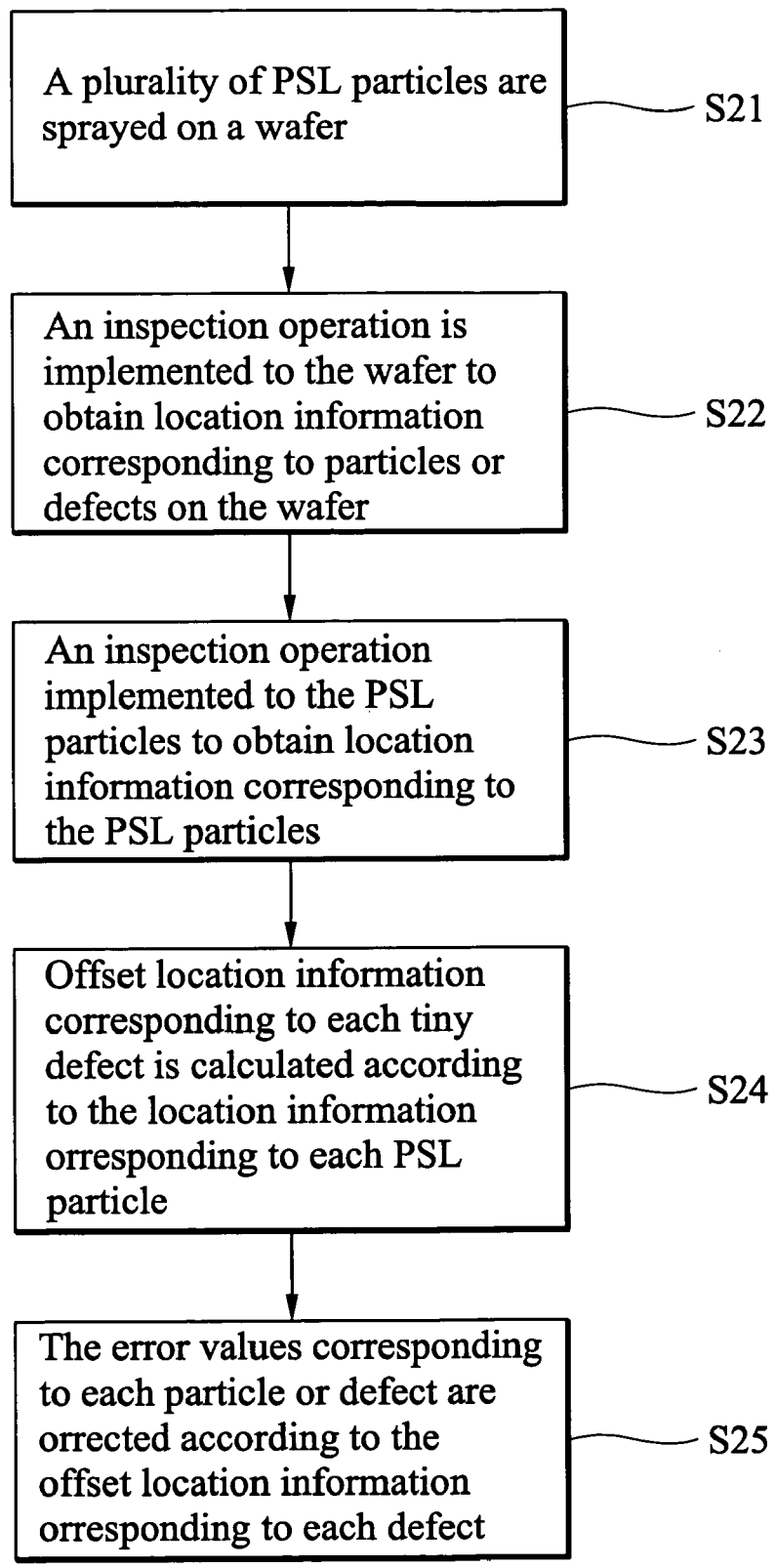
FIG. 2 is a flowchart of an embodiment of a wafer defect detection method.

FIG. 2 is a flowchart of an embodiment of a wafer defect detection method.

A plurality of PSL particles, each between 0.3~0.5 um, are sprayed on a wafer (step S21). An inspection operation is implemented on the wafer to obtain location information corresponding to particles or defects on the wafer (step S22), each location information corresponding to the particles or defects comprising an error value. Next, an inspection operation is implemented on the PSL particles to obtain location information corresponding to the PSL particles (step S23).

The size of a PSL particle, between 0.3~0.5 um, confirms to the hardware limitations of a tool, and is able to obtain more accurate location information. When location information corresponding to the PSL particles is obtained, offset location information corresponding to each tiny (less than 100 nm) particle or defect is calculated according to the location information corresponding to each PSL particle (step S24). The error values corresponding to each particle or defect are corrected according to the offset location information corresponding to each particle or defect to estimate real locations requiring implementation of a defect repair process (step S25).

Figure 3:
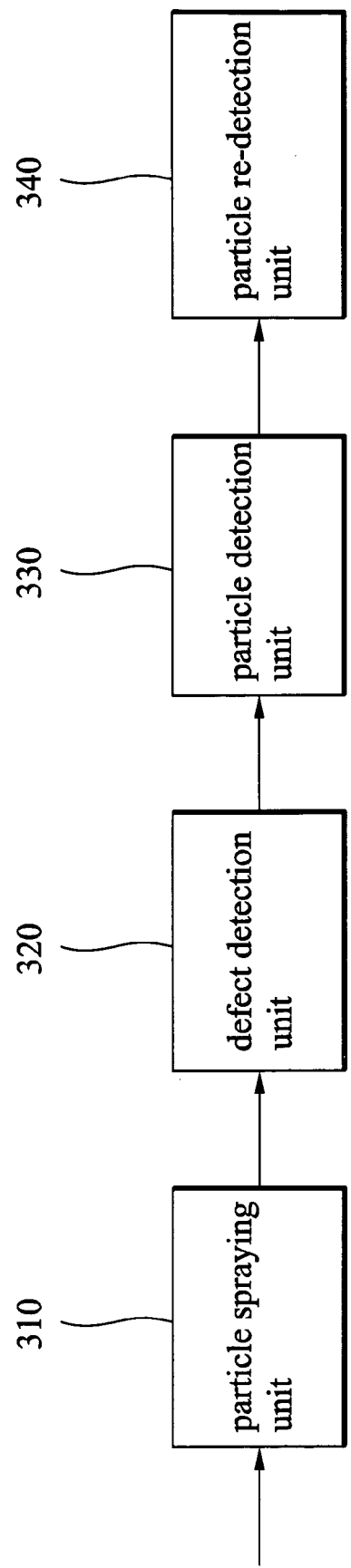
FIG. 3 is a schematic view of an embodiment of a wafer defect detection system.

FIG. 3 is a schematic view of an embodiment of a wafer defect detection system.

A wafer defect detection system 300 of the invention comprises a particle spraying unit 310, a defect detection unit 320, a particle detection unit 330, and a particle re-detection unit 340. Particle spraying unit 310 sprays a plurality of locating particles on a wafer. Defect detection unit 320 implements an inspection operation on the wafer to obtain location information corresponding to a plurality of defects on the wafer, each location information corresponding to the particles or defects comprises an error value. Particle detection unit 330 implements an inspection operation on the PSL particles to obtain location information corresponding to the PSL particles. Particle re-detection unit 340 calculates offset location information corresponding to each tiny (less than 100 nm) particle or defect according to the location information corresponding to each PSL particle, and corrects error values corresponding to each particle or defect according to the offset location information corresponding to each particle or defect to estimate real locations for implementation of a defect repair process accordingly.

The described method for calculating offset location information corresponding to each particle or defect can be achieved using, but is not limited to, mathematical operations. Additionally, locating particles sprayed on a wafer can be, but are not limited to, PSL particles, particles conforming to hardware limitations of a tool are applicable.

Figure 4:
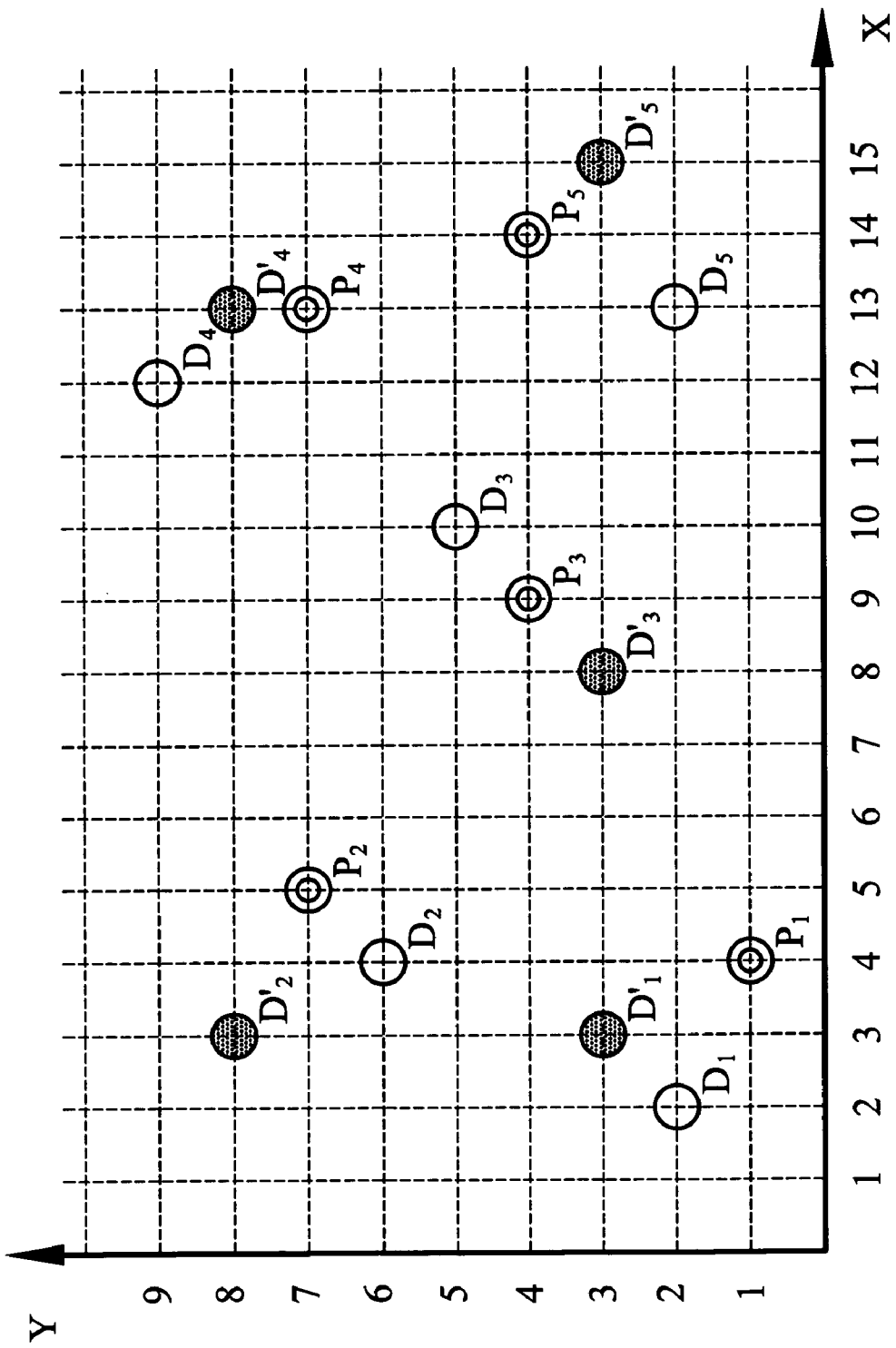
FIG. 4 is a schematic view of an example of wafer defect detection.

FIG. 4 is a schematic view of an example of a wafer defect detection.

Based on the described detection method and system, an example is illustrated. Referring to FIG. 4, PSL particles are sprayed on a wafer (step S21) and the wafer is scanned and inspected to obtain location information of defects $D_1'\sim D_5'$, comprising $D_1'$ (3,3), $D_2'$ (3,8), $D_3'$ (8,3), $D_4'$ (13,8), and $D_5'$ (15,3). Location information of real defects $D_1\sim D_5$ comprises $D_1$(2,2), $D_2$(4,6), $D_3$(10,5), $D_4$(12,9), and $D_5$(13,2). Real defects $D_1\sim D_5$ are tiny and correct locations cannot be detected, such that coordinates of divergent defects $D_1'\sim D_5'$ are detected. An error value is added to each coordinate of defects $D_1\sim D_5$ equal to each coordinate of defects $D_1'\sim D_5'$. In this embodiment, tiny defects (less than 100 nm) are given as an example, other defects may be detected using general detection methods are not described for simplificity.

Next, sprayed PSL particles $P_1\sim P_5$ are scanned and inspected, thus obtaining coordinates thereof, comprising $P_1$ (2,2), $P_2$(4,6), $P_3$(10,5), $P_4$(12,9), and $P_5$(13,2) (step S23). Offset location information corresponding to defects $D_1\sim D_5$ and defects $D_1'\sim D_5'$ is calculated according to the coordinates corresponding to PSL particles $P_1\sim P_5$ (step S24). Offset of PSL particle $P_1$, for example, relative to defects $D_1$ and defects $D_1'$, respectively, is identical, but, relative to the X-axis and Y-axis corresponding to defects $D_1$ and defects $D_1'$, respectively, is different. Error values corresponding to defect $D_1'\sim D_5'$ are corrected according to the offset corresponding to the defects $P_1\sim P_5$ to estimate real coordinates for implementation of a defect repair process (step S25).

A wafer defect detection method of the invention detects relative locations of defects and then corrects error values corresponding thereto using PSL particles, thus obtaining real locations to increase inspection success rates.

Although the present invention has been described in terms of preferred embodiment, it is not intended to limit the invention thereto. Those skilled in the technology can still make various alterations and modifications without departing from the scope and spirit of this invention. Therefore, the scope of the present invention shall be defined and protected by the following claims and their equivalents.

What is claimed is:

1. A wafer defect detection method, comprising:
   spraying a plurality of locating particles on a wafer;
   implementing an inspection operation on the wafer to obtain location information corresponding to a plurality of defects on the wafer, wherein each location information corresponding to the defects comprises an error value;
   implementing an inspection operation on the locating particles to obtain location information corresponding to the locating particles;
   calculating offset location information corresponding to each defect according to the location information corresponding to each locating particle; and
   correcting error values corresponding to each defect according to the offset location information corresponding to each defect.

2. The wafer defect detection method as claimed in claim 1, wherein the locating particles are PSL particles.

3. The wafer defect detection method as claimed in claim 1, wherein the size of each defect size is less than 100 nm.

4. A wafer defect detection method, comprising:
   spraying a plurality of locating particles on a wafer;
   implementing an inspection operation on the wafer to obtain location information corresponding to a plurality of defects on the wafer, wherein each location information corresponding to the defects comprises an error value;
   implementing an inspection operation on the locating particles to obtain location information corresponding to the locating particles;
   calculating offset location information corresponding to error defect location and real defect location information relating to each defect according to the location information corresponding to each locating particle; and
   correcting error values corresponding to each defect according to the offset location information.

5. The wafer defect detection method as claimed in claim 4, wherein the locating particles are PSL particles.

6. The wafer defect detection method as claimed in claim 4, wherein the size of each defect is less than 100 nm.

7. A wafer defect detection system, comprising:
   a particle spraying unit, spraying a plurality of locating particles on a wafer;
   a defect detection unit, coupled to the particle spraying unit, implementing an inspection operation on the wafer to obtain location information corresponding to a plurality of defects on the wafer, wherein each location information corresponding to the defects comprises an error value;

a particle detection unit, coupled to the defect detection unit, implementing an inspection operation on the locating particles to obtain location information corresponding to the locating particles; and a particle re-detection unit, coupled to the particle detection unit, calculating offset location information corresponding to each defect according to the location information corresponding to each locating particle, and correcting error values corresponding to each defect according to the offset location information corresponding to each defect.

8. The wafer defect detection system as claimed in claim 7, wherein the locating particles are PSL particles.

9. The wafer defect detection system as claimed in claim 7, wherein the size of each defect is less than 100 nm.

* * * * *